(12) United States Patent
Della Valle et al.

(10) Patent No.: US 10,441,559 B2
(45) Date of Patent: Oct. 15, 2019

(54) METHOD OF TREATING NEUROPATHIC PAIN WITH A SYNERGISTIC PHARMACEUTICAL COMPOSITION COMPRISING PALMITOYLETHANOLAMIDE AND L-ACETYLCARNITINE

(71) Applicant: EPITECH GROUP S.R.L., Milan (IT)

(72) Inventors: Francesco Della Valle, Milan (IT); Maria Federica Della Valle, Milan (IT)

(73) Assignee: Epitech S.P.A., Milan (IT)

( * ) Notice: Subject to any disclaimer, the term of this patent is extended or adjusted under 35 U.S.C. 154(b) by 9 days.

(21) Appl. No.: 15/603,566

(22) Filed: May 24, 2017

(65) Prior Publication Data

US 2017/0252314 A1   Sep. 7, 2017

Related U.S. Application Data

(63) Continuation of application No. 14/658,369, filed on Mar. 16, 2015, now abandoned.

(30) Foreign Application Priority Data

Mar. 19, 2014 (IT) .............................. MI2014A0454

(51) Int. Cl.
| | |
|---|---|
| *A61K 31/221* | (2006.01) |
| *A61K 31/164* | (2006.01) |
| *A61K 31/7034* | (2006.01) |
| *A61K 9/00* | (2006.01) |
| *A61K 9/16* | (2006.01) |

(52) U.S. Cl.
CPC .......... *A61K 31/221* (2013.01); *A61K 9/0024* (2013.01); *A61K 9/1647* (2013.01); *A61K 31/164* (2013.01); *A61K 31/7034* (2013.01)

(58) Field of Classification Search
USPC ...................................................... 424/489
See application file for complete search history.

(56) References Cited

U.S. PATENT DOCUMENTS

| | | |
|---|---|---|
| 5,973,004 A | 10/1999 | Howard |
| 5,990,170 A | 11/1999 | Della Valle et al. |
| 6,548,550 B1 | 4/2003 | Comelli et al. |
| 8,470,373 B2 | 6/2013 | Della Valle et al. |
| 8,663,701 B2 | 3/2014 | Della Valle et al. |
| 2011/0171313 A1 | 7/2011 | Della Valle et al. |

FOREIGN PATENT DOCUMENTS

WO   2011/027373 A1   3/2011

OTHER PUBLICATIONS

S. Chiechio et al: "L-Acetylcarnitine: A Proposed Therapeutic Agent for Painful Peripheral Neuropathies", Current Neuropharmacology, Vo. 4, No. 3, Jul. 1, 2006, pp. 233-237, See Italian Search.
Chiechio Santina et al: "Acetyl-L-Carnitine in Neuropathic Pain", CNS Drugs, Adis International, Auckland NZ, vol. 21, No. Suppl. 1, Jan. 1, 2007, pp. 31-38, See Italian Search.
Gatti Antonio et al: "Palmitoylethanolamide in the Treatment of Chronic Pain Caused by Different Etiopathogenesis", Pain Medicine, Sep. 2012, Vo. 13, No. 9, pp. 1121-1130, See Italian Search.
Hesselink J M K: "New Targets in Pain, Non-Neuronal Cells, and the Role of Palmitoylethanolamide", Open Pain Journal 2012, Bentham Science Publishers B.V. NLD, vol. 5, No. 1, pp. 12-23, See Italian Search.
Indraccolo U et al: "Effect of Palmitoylethanolamide-polydatin Combination of Chronic Pelvic Pain Associated with Endometriosis: Preliminary Observations", European Journal of Obstetrics & Gynecology and Reproductive Biology, Excerpta Medica, Amsterdam, NL, vol. 150, No. 1, May 2010, pp. 76-79, See Italian Search.
Gilron et al: "Morphine, Gabapentin, or Their Combination for Neuropathic Pain", The New England Journal of Medicine, 352;13, Mar. 31, 2005, pp. 1324-1334.
Gilron et al: "Nortriptyline and gabapentin, alone and in combination for neuropathic pain: a double-blind, randomised controlled crossover trial", The Lancet, vol. 374, Oct. 10, 2009, pp. 1252-1261.
Sima et al: "Acetyl-L-Carnitine Improves Pain, Nerve Regeneration, and Vibratory Perception in Patients with Chronic Diabetic Neuropathy", Diabetes Care, vol. 28, No. 1, Jan. 2005, pp. 89-94.
Vorobeychik et al: "Combination Therapy for Neuropathic Pain" CNS Drugs, vol. 25, Issue 12, Dec. 2011, pp. 1023-1034.
Treede et al: "Neuropathic Pain: Redefinition an da grading system for clinical research purposes", Neurology, vol. 70, 2008, pp. 1630-1635.
Italian Search Report Corresponding to MI20140454 dated Oct. 9, 2014.

*Primary Examiner* — Devang K Thakor
(74) *Attorney, Agent, or Firm* — Davis & Bujold PLLC; Michael J. Bujold

(57) ABSTRACT

A method of controlling the inflammatory and/or neuropatic pain of various origins by administering a pharmaceutical composition containing palmitoylethanolamide, to a human or animal patient. In particular, the present invention relates to the administration of a pharmaceutical composition comprising palmitoylethanolamide (PEA) and L-acetylcarnitine (LAC), optionally in addition with an antioxidant compound, such as a polyphenol, alpha-lipoic acid, or L-acetylcysteine to a patient.

16 Claims, 1 Drawing Sheet

— Mechanical allodunia determined after stimles following scietic nerve litigation in mouse.

|  | Control/vehicle | CCI/vehicle | CCI/LAC 100mg/kg | CCI/LAC 10mg/kg | CCI/PEA-um 10mg/kg | CCI/PEA-um 5mg/kg | CCI/PEA-um 5mg/kg /LAC10mg/kg | CCI/PEA 5mg/kg co-micronized with polydetina 0,5 mg/kg /LAC 10 mg/kg |
|---|---|---|---|---|---|---|---|---|
| Day 0 | 5,0 | 5,0 | 5,0 | 5,0 | 5,0 | 5,0 | 5,0 | 5,0 |
| Day 4 | 4,9 | 1,3 | 2,8 | 1,4 | 3,5 | 1,8 | 4,0 | 4,6 |
| Day 8 | 4,9 | 1,2 | 3,3 | 1,7 | 4,0 | 2,2 | 4,4 | 4,8 |

METHOD OF TREATING NEUROPATHIC PAIN WITH A SYNERGISTIC PHARMACEUTICAL COMPOSITION COMPRISING PALMITOYLETHANOLAMIDE AND L-ACETYLCARNITINE

CROSS REFERENCE TO RELATED APPLICATIONS

This application is a Continuation of U.S. application Ser. No. 14/658,369, filed Mar. 16, 2015, which claims priority from Italian patent application serial no. MI2014A000454, filed Mar. 19, 2014; the disclosure of each of which is incorporated herein by reference in its entirety.

TECHNICAL FIELD OF THE INVENTION

It is the object of the present invention a pharmaceutical composition for use in humans or animals containing N-palmitoylethanolamide for controlling the inflammatory and/or neuropathic pain of various origins.

BACKGROUND

Today, neurogenic pain, also referred to as inflammatory pain, can be defined as the consequence of a complex multi-factorial mechanism localized in the innervated tissues and/or the miniaturized endoneurial compartment in which, in addition to the nociceptive nerve terminals and/or the axons composing the peripheral sensitive fibers, the endothelial cells of the microcirculation, both tissue and endoneurial mastocytes, and cells of an immunologic nature extravasated from the tissue microcirculation in cases of suffering of the peripheral nervous system and/or of the tissue it innervates are involved. The whole process is defined as neurogenic inflammation, and it gives rise to the phenomenon referred to as peripheral sensitization.

The neuropathic pain, characteristic of neuropathies caused by traumatic, compressive, dysmetabolic, and infective injuries, is characterized by spontaneous pain, allodynia, and hyperalgesia. Today, the "central sensitization" found at the level of the dorsal horns of the spinal cord, generally as a consequence of a lesion or an alteration of the somatosensory nervous system (Neurology 2008; 70:1630-1635), is recognized as the most important mechanism on which of chronic pain is based. In addition to the synaptic junction between the first and second neuron, glial cells and in particular the microglia are involved in this sensitization process. The activation and proliferation of the microglia induced, as stated above, by injury or dysmetabolism of neuronal systems (peripheral, spinal, supraspinal) results in a significant alteration of the synaptic plasticity induced by growth factors of protein origin released by the microglia, with substantial modification of the neurotransmission (peptidergic, glutamatergic) dialogue between the first and second neurons. In particular, the neurotransmission at the level of said synaptic junction is deeply changed, passing from an essentially glutamatergic neurotransmission through NMDA-type receptors to a mixed neurotransmission, glutamatergic—in part still of an NMDA type and in part of a metabotropic type (through a series of glutamatergic receptors belonging to the mGlu family)—and peptidergic, essentially related to the neuropeptide knowns as Substance P (SP).

Since time, it has been known that palmitoylethanolamide, an endogenous lipid of an N-acylethanolamide nature produced on demand in the case of a cell damage, is capable of modulating in an inhibitory manner both the hyperdegranulation of the mastocyte and the hyper-activation of the microglia, thus showing to be capable, when administered in such a pharmaceutical form as to ensure bioavailability at the level of the above-mentioned two target cells, controlling the neuronal—peripheral and central—sensitization and, consequently, both the inflammatory and neuropathic pain. In particular, palmitoylethanolamide showed a particularly relevant effect, at the dose of 10 mg/kg, in the neuropathic pain model obtained by sciatic nerve ligation in the mouse; clinically, many studies proved the ability of palmitoylethanolamide, administered p.o. in an appropriate form—e.g., micronized and/or ultra-micronized—of reducing both inflammatory pain and chronic and neuropathic pain associated with several disease conditions.

L-Acetylcarnitine (LAC), a molecule which is typically used in the treatment of painful neuropathies, proved to be able, at a dose of 100 mg/kg, to decrease the mechanical allodynia in the neuropathic pain model obtained by sciatic nerve ligation in rodents (CCI). The mechanism of action of such molecule is a selective over-regulation of the metabotropic receptors for glutamate, and in particular of the receptor referred to as mGlu2 at the level of the joint between the first and the second neurons, located in the posterior horns of the spinal cord.

SUMMARY OF THE INVENTION

The inventors of the present patent have surprisingly found that the association between palmitoylethanolamide, in micronized or ultramicronized form, and L-acetylcarnitine is capable of providing a highly synergic effect between the two molecules, which effect is particularly clearance of neuropathic pain.

They have further found that the addition of a molecule with antioxidative activity to the association between palmitoylethanolamide and L-acetylcarnitine—optionally co-micronized with palmitoylethanolamide—further enhances the synergy between the two main components of the invention.

Therefore, an object of the present invention is administration of a pharmaceutical composition comprising palmitoylethanolamide (PEA), alternatively in non-micronized form (non-micronized PEA), or in micronized form (PEA-m), or in ultra-micronized form (PEA-um), and L-acetylcarnitine in finely pulverized form.

A further object of the invention is administration of a pharmaceutical composition comprising palmitoylethanolamide (PEA) as defined above, L-acetylcarnitine, and antioxidative molecules of the polyphenols family (e.g., polydatin, resveratrol, luteolin, quercetin, rutin, etc.), α-lipoic acid, and/or acetylcysteine.

The invention is defined by the appended claims.

Further characteristics and advantages of the process according to the invention will be apparent from the description set forth below of preferred embodiments, given by way if illustrative, non-limiting example.

BRIEF DESCRIPTION OF THE DRAWINGS

FIG. 1 shows a Table illustrating the data regarding a mechanical allodynia test following a sciatic nerve ligation in mouse.

DETAILED DESCRIPTION OF THE INVENTION

The invention relates to the use of a pharmaceutical composition comprising palmitoylethanolamide (PEA), alternatively in non-micronized form (non-micronized PEA), or in micronized form (PEA-m), or in ultra-micronized form (PEA-um), and L-acetylcarnitine in finely pulverized form.

Palmitoylethanolamide can be synthetized as described in Example no. 25 of U.S. Pat. No. 5,990,170.

Non-micronized PEA can be obtained by finely grounding the product from the synthesis; product with a particle size ranging between 50.0 and 100.0 µm can be obtained.

PEA-m can be obtained as described in the U.S. Pat. No. 6,548,550 B1 and it has a particle size ranging between 2.0 and 10.0 µm.

PEA-um can be obtained as described in the patent Application PCT issued with no. WO 2011/027373 A1 and it has a particle size ranging between 0.8 and 6.0 µm.

More indications on said forms of PEA are present in the above-mentioned patent publications, the content of which relating to the characterization of the product is incorporated herein by reference.

Pharmaceutical grade L-acetylcarnitine is a commercially available product.

The pharmaceutical composition of the invention comprises palmitoylethanolamide in weight percentages ranging between 20 and 35%, L-acetylcarnitine in weight percentages between 20 and 55%, and one or more compounds with antioxidant activity total weight percentages ranging between 0 and 20%.

The compound with antioxidant activity is preferably selected from the group comprising polyphenols, alpha-lipoic acid (or thioctic acid), and the L-acetylcysteine.

When the antioxidant compound is or comprises a polyphenol, it is preferably selected polydatin, resveratrol, luteolin, quercetin and rutin.

The molecules having an antioxidative activity may also be co-micronized with palmitoylethanolamide according to the teachings described in U.S. Pat. No. 6,548,550 E1.

The antioxidative compounds are commercially available products.

The inventive composition can further contain pharmaceutically acceptable excipients and additives, selected as a function of the desired pharmaceutical form.

The diseases which can be treated with the composition of the present invention comprise:

Both acute and chronic painful peripheral neuropathies of dysmetabolic, compressive, traumatic, toxic, infectious, iatrogenic origin;

Pain associated with vertebral column and spinal cord diseases of traumatic, dysmetabolic, degenerative, infectious, iatrogenic origin;

Pain associated with small fiber diseases of infectious, traumatic, dysmetabolic, iatrogenic origin;

Acute and/or chronic pain associated with diseases in the pelvic area, such as Endometriosis, Interstitial Cystitis, Recurrent Cystitis, Irritable Bowel Syndrome, Prostatites, Vaginites, Vulvovaginites, primary and secondary Dysmenorrhoea, Vulvodynias, Vestibulodynias;

Pain associated with traumatic and degenerative joint diseases; and

Pain associated with arthritic diseases.

The pharmaceutical composition according to the present invention can be formulated for an oral, a buccal, or a rectal administration.

For the oral administration, the pharmaceutical compositions can be, for example, in the form of tablets or capsules prepared in a conventional manner with pharmaceutically acceptable excipients, such as binders (e.g., pre-gelatinized corn starch, polyvinylpyrrolidone, or hydroxypropyl methylcellulose); filling agents (e.g., lactose, microcrystalline cellulose or calcium hydrogen phosphate); lubricants (e.g., magnesium stearate, talc, or silica); disintegrating agents (e.g., potato starch or sodium starch glycolate); or inhibiting agents (e.g., sodium lauryl sulfate). The tablets can be coated by methods well known in the art. The liquid preparations for oral administration can be, for example, in the form of solutions, syrups or suspensions, or they can be in the form of lyophilized products to be reconstituted, before their use, with water or other suitable vehicles. Such liquid preparations can be prepared by conventional methods with pharmaceutically acceptable additives, such as suspending agents (e.g., sorbitol syrup, cellulose derivatives, or edible hydrogenated fats); emulsifying agents (e.g., lecithin or acacia); non-aqueous vehicles (e.g., almond oil, oily esters, ethyl alcohol, or fractionated plant-based oils); and preservatives (e.g., methyl- or propyl-p-hydroxybenzoates or sorbic acid). The preparation may also suitably contain flavors, colorants, and sweeteners.

The preparations for oral administration can be suitably formulated to allow the controlled release of the active ingredient.

For the buccal administration, the compositions can be in the form of tablets or lozenges formulated in a conventional manner, suitable for an absorption by the buccal mucosae. Typical buccal formulations are the tablets for sub-lingual administration.

According to the present invention, the compounds can also be formulated in rectal compositions, such as suppositories or retention enema, for example containing the base components of typical suppositories, such as cocoa butter or other glycerides.

In addition to the compositions described above, the compounds can also be formulated as depot preparations. Such long-acting formulations can be administered by an implant (for example, subcutaneously, transdermally, or intramuscularly) or by intramuscular injection. Thus, for example, the compounds, according to the present invention, can be formulated with suitable polymeric or hydrophobic materials (e.g., in the form of an emulsion in a suitable oil) or ionic exchange resins, or as minimally soluble derivatives, for example, as a minimally soluble salt.

According to the present invention the dose of the compounds proposed for the administration to a human being (with a body weight of about 70 Kg) ranges from 10 mg to 1 g, and preferably from 100 mg to 500 mg of the active ingredients per dose unit. The dose unit can be administered, for example, 1 to 4 times/day. The dose will depend on the selected administration route. It shall be considered that it could be necessary to continuously vary the dosage as a function of the age and weight of the patient, and also of the severity of the clinical condition to be treated. Finally, the precise dose and the administration route will be at discretion of the attending physician or veterinary.

The formulations described above can be prepared according to conventional methods, such as those described in Remington's Pharmaceutical Sciences Handbook, Mack Pub. Co., N.Y., USA.

Experimental Section

Experimental Model of Neuropathic Pain

The experiments were carried out using male mice the C57BL/6J strain with a weight ranging between 25 and 30 g; 10 animals per group were used. The animals were anesthetized with sodium pentobarbital (60 mg/kg, i.p.) and subjected to a surgical procedure of sciatic nerve ligation capable of inducing neuropathic pain in accordance with the method described by Bennet and Xie (1988, Pain; 33:87-107). Sham animals were used as a control.

The products were administered p.o. with a tube, suspended in 2% Carboxymethyl Cellulose.

The mechanical allodynia was measured by using the Dynamic Plantar Aesthesiometer equipment of the Company Ugo Basile—Varese, Italy.

Data are set forth in Table of FIG. 1. The values in the table are referred to the weight, expressed in grams, to which the animal object of the experiment, subjected thereto, withdraws its paw when feeling pain. It is pointed out from the data set forth in the table that LAC alone or PEA-um alone cause a significant alleviation of the neuropathic pain when used at doses, of 100 mg/kg and 10 mg/kg, respectively, while, at a dose of 10 mg/kg for LAC alone and of 5 mg/kg for PEA-um alone, the two substances do not cause a significant activity.

Vice versa, PEA-um at a dose from 5 mg/kg in association with LAC at a dose of 10 mg/kg, causes a very high decrease of the neuropathic pain after 8 days of treatment.

Finally, the association of PEA (5 mg/kg) co-micronized with polydatin (0.5 mg/kg) and in association with LAC (10 mg/kg) cause an almost complete remission of neuropathic pain after 8 days of treatment.

Therefore, data show a markedly synergic effect of the combination of PEA, in particular PEA-um, and LAC, above all when in association with an antioxidant.

The invention will be now further described by some formulation examples, given by way of exemplary, non-limiting examples of the protection scope of the invention as defined by the appended claims.

FORMULATION EXAMPLES

Example A

Tablets for Oral Use

Each tablet contains:
150.0 mg PEA-um
300.0 mg LAC
80.0 mg Microcrystalline Cellulose
45.0 mg Croscarmeilose Sodium
10.0 mg Polyvinylpyrrolidone
4.0 mg Magnesium Stearate Example B Tablets for Oral Use Each tablet contains:
200.0 mg PEA-m
300.0 mg LAC
90.0 mg Microcrystalline Cellulose
65.0 mg Croscarmellose Sodium
15.0 mg Polyvinylpyrrolidone
4.0 mg Magnesium Stearate Example C Tablets for Oral Use Each tablet contains:
200.0 mg PEA-m (co-micronized with Polydatin)
20.0 mg Polydatin (co-micronized with PEA-m)
300.0 mg LAC
90.0 mg Microcrystalline Cellulose
65.0 mg Croscarmellose Sodium
15.0 mg Polyvinylpyrrolidone
4.0 mg Magnesium Stearate Example D Tablets for Oral Use Each tablet contains:
200.0 mg PEA-m (co-micronized with Quercetin)
25.0 mg Quercetin (co-micronized with PEA-m)
300.0 mg LAC
90.0 mg Microcrystalline Cellulose
mg 65.0 Croscarmellose Sodium
15.0 mg Polyvinylpyrrolidone
4.0 mg Magnesium Stearate Example E Tablets for Oral Use Each tablet contains:
200.0 mg PEA-um
50.0 mg Acetylcysteine
300.0 mg LAC
90.0 mg Microcrystalline Cellulose
65.0 mg Croscarmellose sodium
15.0 mg Polyvinylpyrrolidone
4.0 mg Magnesium Stearate Example F Tablets for Oral Use Each tablet contains:
150.0 mg PEA-m
100.0 mg α-Lipoic Acid
200.0 mg LAC
100.0 mg Microcrystalline Cellulose
80.0 mg Croscarmellose sodium
10.0 mg Polyvinylpyrrolidone
15.0 mg Magnesium. Stearate Example G Microgranules for Sublingual Use Each sachet of microgranules contains:
300.0 mg PEA-um
100.0 mg Acetylcysteine
300.0 mg LAC
380.0 mg Sorbitol powder
15.0 mg Saccharose Palmitate
5.0 mg Polysorbate 80 (plant-based).

What is claimed:
1. A method of treating neuropathic pain, comprising:
administering to a patient a synergistic pharmaceutical daily dosage form comprising:
palmitoylethanolamide (PEA), and
L-acetylcarnitine (LAC) in a finely pulverized form; and
the pharmaceutical daily dosage form is for oral or buccal use, and palmitoylethanolamide (PEA) and L-acetyl-carnitine (LAC) are contained in the daily dosage form in doses not exceeding 5 mg/kg of the palmitoylethanolamide (PEA) and not exceeding 10 mg/kg of L-acetylcarnitine (LAC);
wherein the pharmaceutical daily dosage form has palmitoylethanolamide in a weight percentage between 20 and 35%, L-acetylcarnitine in a weight percentage between 20 and 55% and one or more compounds with antioxidant activity in a total weight percentage ranging between 0 and 20%, and
a combination of the palmitoylethanolamide, the L-acetylcarnitine and the one or more compounds with antioxidant activity does not exceed a weight percent of 100%.

2. The method of claim 1, wherein the one or more compounds with the antioxidant activity is selected from the group consisting of polyphenols, alpha-lipoic acid, and L-acetylcysteine.

3. The method of claim 2, wherein the one or more compounds with the antioxidant activity, comprises a polyphenol selected from the group consisting of polydatin, resveratrol, luteolin, quercetin, and rutin.

4. The method of claim 1, wherein the synergistic pharmaceutical daily dosage form further comprises:
an active dosage of palmitoylethanolamide in an amount of 5 mg/kg;
an active dosage of L-acetylcarnitine in an amount of 10 mg/kg; and
an active dosage of the one or more compounds with an antioxidant activity in an amount of about 0.5 mg/kg such that the synergistic pharmaceutical daily dosage form is one of a dosage tablet, a capsule, or liquid form of a pharmaceutical composition.

5. The method of claim 1, wherein the one or more compounds with the antioxidant activity is co-micronized with the palmitoylethanolamide.

6. The method of claim 1, wherein the neuropathic pain results from a disease selected from:
both acute and chronic painful peripheral neuropathies of dysmetabolic, compressive, traumatic, toxic, infectious, iatrogenic origin;
pain associated with vertebral column and spinal cord diseases of traumatic, dysmetabolic, degenerative, infectious, iatrogenic origin;
pain associated with small fibre diseases of infectious, traumatic, dysmetabolic, iatrogenic origin;
acute and/or chronic pain associated with diseases in the pelvic area, such as Endometriosis, Interstitial Cystitis, Recurrent Cystitis, Irritable Bowel Syndrome, Prostatites, Vaginites, Vulvovaginites, primary and secondary Dysmenorrhoea, Vulvodynias, Vestibulodynias;
pain associated with traumatic and degenerative joint diseases; and
pain associated with arthritic diseases.

7. The method of claim 4, wherein the pharmaceutical composition is for human or veterinary use.

8. The method of claim 1, wherein the palmitoylethanolamide is in ultra-micronized form (PEA-um) with a particle size ranging between 0.8 and 6.0 microns.

9. A method of treating neuropathic pain, comprising:
administering to a patient a dosage tablet, a capsule, or a liquid form of a synergistic pharmaceutical composition, wherein each dosage tablet, capsule, or liquid form of the pharmaceutical composition comprises:
an active dosage of palmitoylethanolamide in an amount not to exceed 5 mg/kg;
an active dosage of L-acetylcarnitine in an amount not to exceed 10 mg/kg; and
an active dosage of one or more compounds with an antioxidant activity in an amount not to exceed 0.5 mg/kg such that each dosage tablet, capsule, or liquid form of the synergistic pharmaceutical composition has palmitoylethanolamide in weight percentages ranging between 20 and 35%, L-acetylcarnitine in weight percentages between 20 and 55%, and the one or more compounds with the antioxidant activity in total weight percentages not to exceed 20%,
wherein the combination of palmitoylethanolamide, L-acetylcarnitine and the one or more compounds with the antioxidant activity does not exceed a weight percent of 100% and a combined amount of palmitoylethanolamide (PEA) and L-acetylcarnitine (LAC) does not exceed about 1 g per each dosage tablet, capsule, or liquid form of the pharmaceutical composition.

10. The method of claim 9, wherein said palmitoylethanolamide is in non-micronized form with a particle size ranging between 50.0 and 100.0 μm, in micronized form (PEA-m) with a particle size ranging between 2.0 and 10.0 μm, or in ultra-micronized form (PEA-um) with a particle size ranging between 0.8 and 6.0 μm, or in a mixture of such forms.

11. The method of claim 10, wherein said L-acetylcarnitine is in a finely pulverized form.

12. The method of claim 9, wherein the one or more compounds with the antioxidant activity is selected from the group consisting of polyphenols, alpha-lipoic acid, and L-acetylcysteine.

13. The method of claim 9, wherein the one or more compounds with the antioxidant activity, comprises a polyphenol selected from the group consisting of polydatin, resveratrol, luteolin, quercetin, and rutin.

14. The method of claim 10, wherein the one or more compounds with the antioxidant activity is co-micronized with palmitoylethanolamide.

15. The method of claim 9, wherein the pharmaceutical composition is for human or veterinary use.

16. The method of claim 9, wherein the neuropathic pain results from a disease selected from:
both acute and chronic painful peripheral neuropathies of dysmetabolic, compressive, traumatic, toxic, infectious, iatrogenic origin;
pain associated with vertebral column and spinal cord diseases of traumatic, dysmetabolic, degenerative, infectious, iatrogenic origin;
pain associated with small fibre diseases of infectious, traumatic, dysmetabolic, iatrogenic origin;
acute and/or chronic pain associated with diseases in the pelvic area, such as Endometriosis, Interstitial Cystitis, Recurrent Cystitis, Irritable Bowel Syndrome, Prostatites, Vaginites, Vulvovaginites, primary and secondary Dysmenorrhoea, Vulvodynias, Vestibulodynias;
pain associated with traumatic and degenerative joint diseases; and
pain associated with arthritic diseases.

* * * * *